United States Patent
Sheehy et al.

(10) Patent No.: US 12,279,823 B2
(45) Date of Patent: Apr. 22, 2025

(54) BINOCULAR RETINAL IMAGING DEVICE, SYSTEM, AND METHOD FOR TRACKING FIXATIONAL EYE MOTION

(71) Applicant: C. Light Technologies, Inc., Berkeley, CA (US)

(72) Inventors: Christy Sheehy, San Francisco, CA (US); Zachary Helft, Berkeley, CA (US); Andrew Norton, Woodside, CA (US); Taylor Page, Suffield, CT (US); Michael Simonsen, Rochester, NY (US); Yun Hui Ni, Rochester, NY (US)

(73) Assignee: C. Light Technologies, Inc., Medford, MA (US)

( * ) Notice: Subject to any disclaimer, the term of this patent is extended or adjusted under 35 U.S.C. 154(b) by 0 days.

(21) Appl. No.: 18/243,076

(22) Filed: Sep. 6, 2023

(65) Prior Publication Data

US 2024/0090764 A1    Mar. 21, 2024

Related U.S. Application Data

(63) Continuation of application No. 17/548,432, filed on Dec. 10, 2021, now Pat. No. 11,779,212, which is a
(Continued)

(51) Int. Cl.
*A61B 3/13*    (2006.01)
*A61B 3/00*    (2006.01)
(Continued)

(52) U.S. Cl.
CPC .......... *A61B 3/132* (2013.01); *A61B 3/0008* (2013.01); *A61B 3/1025* (2013.01); *A61B 3/113* (2013.01);
(Continued)

(58) Field of Classification Search
CPC ..... A61B 3/132; A61B 3/0008; A61B 3/1025; A61B 3/113; A61B 3/11; A61B 3/08; G02B 27/0994; G02B 27/14; G02B 27/30
(Continued)

(56) References Cited

U.S. PATENT DOCUMENTS

| 4,783,137 A | 11/1988 | Kosman et al. |
| 5,543,866 A * | 8/1996 | Van de Velde ...... A61B 3/1025 351/205 |

(Continued)

OTHER PUBLICATIONS

PCT/US2017/066506; International Search Report and Written Opinion; Mar. 8, 2018; 13 pp.

*Primary Examiner* — Mohammed A Hasan
(74) *Attorney, Agent, or Firm* — Resonance IP Law, PC

(57) ABSTRACT

A binocular scanning laser ophthalmoscope (SLO) is used to track the fixational eye movement of each of the eyes of a subject. The binocular SLO may include right eye optics for imaging a portion of the retina of the right eye and left eye optics for imaging a portion of the retina of the left eye. Shifts in the imaged portion of the retina with respect to a reference image of the retina may be used to measure and track eye movement. The right eye optics and left eye optics may be separate imaging paths, each with its own bi-directional MEMS scanning mirror and Keplerian telescope. The use of the MEMS scanning mirrors minimizes the size and weight of the binocular SLO.

18 Claims, 8 Drawing Sheets

Related U.S. Application Data continuation of application No. 16/470,038, filed as application No. PCT/US2017/066506 on Dec. 14, 2017, now Pat. No. 11,197,607.

(60) Provisional application No. 62/501,480, filed on May 4, 2017, provisional application No. 62/433,952, filed on Dec. 14, 2016.

(51) Int. Cl.
*A61B 3/10* (2006.01)
*A61B 3/113* (2006.01)
*G02B 27/09* (2006.01)
*G02B 27/14* (2006.01)
*G02B 27/30* (2006.01)

(52) U.S. Cl.
CPC ......... *G02B 27/0994* (2013.01); *G02B 27/14* (2013.01); *G02B 27/30* (2013.01)

(58) Field of Classification Search
USPC .......................................................... 351/205
See application file for complete search history.

(56) References Cited

U.S. PATENT DOCUMENTS

| | | | | |
|---|---|---|---|---|
| 6,820,979 | B1 * | 11/2004 | Stark | A61B 3/112 |
| | | | | 351/206 |
| 8,403,490 | B2 * | 3/2013 | Sugiyama | G02B 26/06 |
| | | | | 359/630 |
| 9,149,182 | B2 * | 10/2015 | Walsh | A61B 5/0022 |
| 11,197,607 | B2 | 12/2021 | Sheehy et al. | |
| 11,779,212 | B2 * | 10/2023 | Sheehy | A61B 3/1025 |
| | | | | 351/205 |
| 2007/0200927 | A1 * | 8/2007 | Krenik | A61B 3/0033 |
| | | | | 348/47 |
| 2009/0244485 | A1 * | 10/2009 | Walsh | A61B 3/0033 |
| | | | | 351/221 |
| 2011/0299034 | A1 * | 12/2011 | Walsh | A61B 3/132 |
| | | | | 351/206 |
| 2012/0203086 | A1 * | 8/2012 | Rorabaugh | A61B 5/0068 |
| | | | | 600/321 |
| 2016/0007849 | A1 * | 1/2016 | Krueger | A61B 5/1128 |
| | | | | 600/301 |
| 2017/0332899 | A1 * | 11/2017 | Walsh | A61B 3/113 |

\* cited by examiner

BINOCULAR RETINAL IMAGING DEVICE, SYSTEM, AND METHOD FOR TRACKING FIXATIONAL EYE MOTION

RELATED APPLICATION

This application is a Continuation of U.S. Non-Provisional application Ser. No. 17/548,432, filed 10 Dec. 2021, which is a Continuation of U.S. Non-Provisional application Ser. No. 16/470,038, filed 14 Jun. 2019 which is a non-provisional patent application of and claims priority to U.S. Provisional Application No. 62/433,952, filed 14 Dec. 2016, and U.S. Provisional Application No. 62/501,480, filed 4 May 2017.

FIELD OF THE INVENTION

The present invention relates to methods and systems for tracking fixational eye motion, and more particularly relates to simultaneously tracking the fixational eye motion of both eyes of a subject and/or comparing deviations between the fixational eye motion of the left and right eyes in order to determine or assess neurological diseases and/or disorders.

BACKGROUND

When a subject fixates upon a stationary reference point, the eyes of the subject are typically not stationary, but rather exhibit small jerk-like, involuntary motions known as microsaccades. Such motion, as well as other forms of motion that occur when the eyes of a subject are fixated upon a stationary reference point, may be referred to herein as "fixational eye motion." One purpose of fixational eye motion is to move a stimulus projected onto the retinas over dozens to hundreds of photoreceptors of the subject's eyes, helping the subject to better see the stimulus. See, e.g., Sheehy et al. "High-speed, image-based eye tracking with a scanning laser ophthalmoscope," Biomed Optics Express, 2012 Oct. 1; 3(10): 2611-2622. Described herein are system and methods for measuring and analyzing the fixational eye motion of a subject.

SUMMARY OF THE INVENTION

In accordance with one embodiment of the invention, a binocular retinal imaging system (which may be hereinafter referred to as a "binocular system") is used to simultaneously record the fixational eye motion of both eyes of a subject. In a healthy subject, the fixational eye motion of the left and right eyes are substantially in sync (i.e., move in the same direction at the same time). However, in subjects with neurological and neurodegenerative conditions/diseases, the fixational eye motion of the left and right eyes may not always be in sync. For example, the speed of motion of one eye might be faster than the speed of the other eye, the motion of one eye might lag the motion of the other eye, etc.

As such, recordings of the fixational eye motion of both eyes of a subject may be analyzed to, for example, diagnose, prognosticate, and monitor neurological and neurodegenerative conditions/diseases such as, for example, multiple sclerosis, dementia, Parkinson's disease, concussion, Alzheimer's, amyotrophic lateral sclerosis (ALS), chronic traumatic encephalopathy (CTE), and so on. Additionally, or alternatively, fixational eye motion may be analyzed in order to, for example, aid in diagnosis or diagnose whether or not a concussion or other traumatic brain injury traumatic brain injury has occurred and assess the severity of the injury as well as monitor recovery. In some instances, diagnosis of a medical condition may be facilitated by comparing the fixational eye motion of a subject's left and right eye and analyzing differences therebetween (i.e., called a conjugacy comparison). The velocity, peak velocity, amplitude, waveforms, and patternistic properties of waveforms of the fixational eye motion may be analyzed as part of the conjugacy comparison.

The binocular system may be used by, for example, medical professionals, technicians, athletic trainers, coaches, physicians, nurses, etc. In some instances, the binocular system may be used and/or installed at, or near, clinical (e.g., doctor's office), emergency (e.g., in an ambulance) and/or various on-site settings, such as a setting associated with a relatively high risk for traumatic brain injury like an athletic field, gym, military training facility, or workplace so as to, for example, facilitate rapid testing and/or diagnosis of an individual with a suspected brain injury. In an ideal circumstance, a conjugacy comparison is performed on a patient prior to any brain injury to establish a baseline, and then a conjugacy comparison is performed on the same patient after a potential brain injury. Any differences between the baseline conjugacy comparison and the following conjugacy comparison could reveal whether any brain injury is present and if so to what degree. If no baseline of that patient is available, a conjugacy comparison could be compared to baseline data from healthy peers of the patient (e.g., peers with the same sex, age range, etc.). It is noted that comparisons other than conjugacy could be used to diagnose neurological diseases. For example, even if the eyes were to move in sync (i.e., together), there may be differences in the velocity and/or the amplitude of the fixational eye movement before and after a brain injury. These additional changes in the fixational eye movement may also be used to diagnose neurological diseases.

In some instances, the binocular system and/or a portion thereof may be portable. Preferably, the binocular system is robust enough to be transported from one place to another (e.g., by means of a rolling cart, be hand-carried within a case, etc.) without misalignment of the optics or other components. In some instances, a portion of the binocular system used to record the fixational eye motion may be portable. The eye motion may be recorded by the portable portion and communicated at a later time to a computer or other processing device stored in a fixed location for analysis and interpretation. This communication may be facilitated by, for example, a physical communication port and/or wired or wireless transceiver located on the portable portion of the binocular system and/or via wired or wireless communication which may be partially, or wholly, facilitated via communication via the Internet or a cloud computing infrastructure. In many instances, the communication and storage of fixation eye motion is protected by encryption and/or other security measures so as to be, for example, compliant with the Health Insurance Portability and Accountability Act (HIPAA) or other similar regulations.

The portability of the binocular system may assist a medical professional with the administration of a diagnostic test and/or the recording of fixational eye motion shortly after a patient experiences a possible brain injury. When the binocular system (or a portion thereof) is portable, the portable portion may be powered by an onboard battery and/or electrical power cord.

These and other embodiments of the invention are more fully described in association with the drawings below.

DETAILED DESCRIPTION OF THE INVENTION

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. Descriptions associated with any one of the figures may be applied to different figures containing like or similar components/steps. While the sequence diagrams each present a series of steps in a certain order, the order of some of the steps may be changed.

Figure 1:
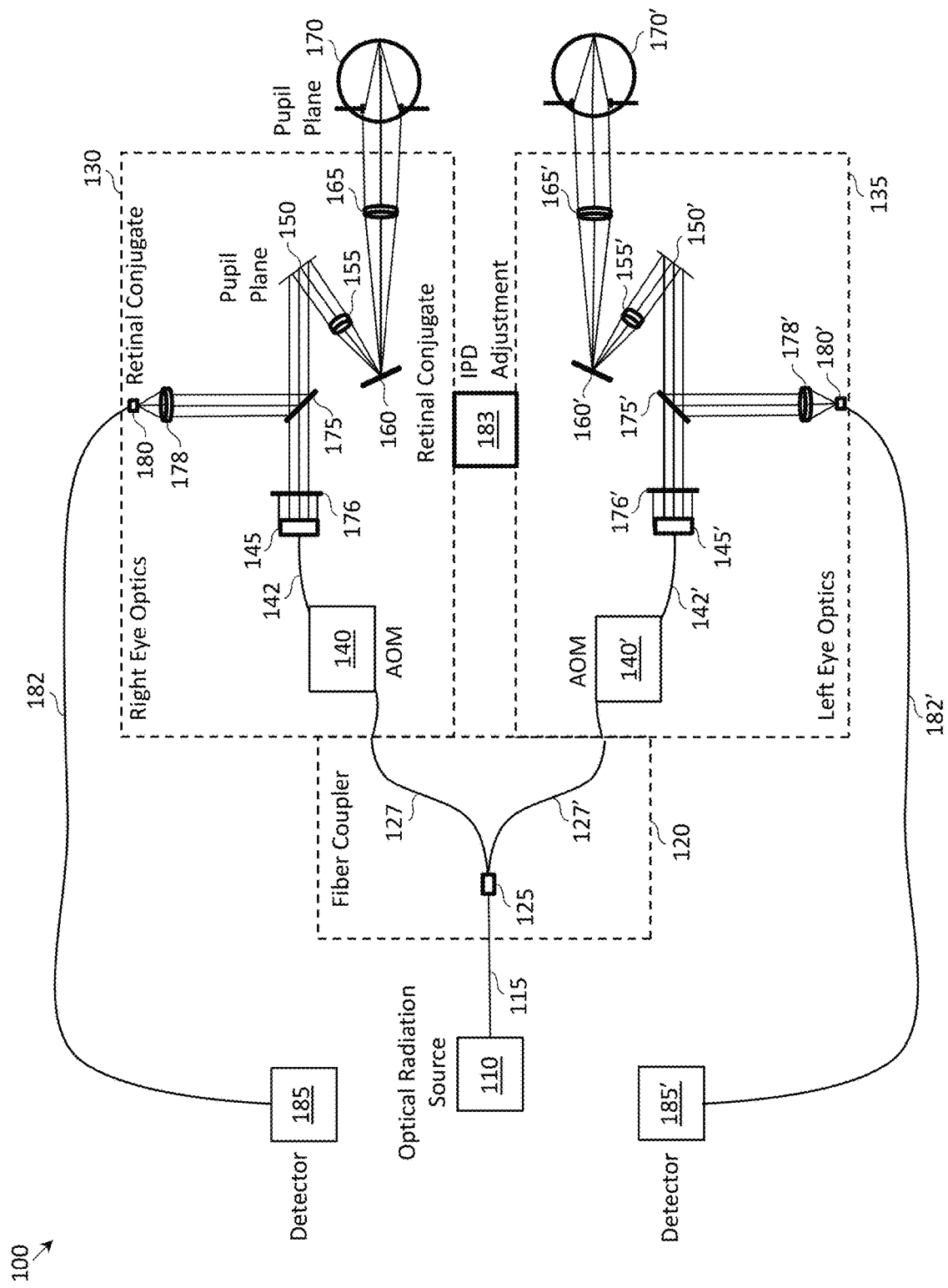
FIG. 1 depicts a binocular scanning laser ophthalmoscope (SLO), in accordance with one embodiment of the invention.

FIG. 1 depicts an example embodiment of binocular scanning laser ophthalmoscope (SLO) 100. In some instances, binocular SLO 100 may be instantiated as a hand-held device and in other instances, binocular system 100 may be embodied in a more permanent installation (e.g., in a doctor's or athletic trainer's office utilizing, for example, a fixed mount).

Binocular SLO 100 may include optical radiation source 110. In one embodiment of the invention, optical radiation source 110 may include a fiber-coupled laser diode configured to emit optical radiation at a single wavelength or nearly the same wavelength. The optical radiation emitted by optical radiation source 110 may be used to raster scan a portion of the retinas of a subject in order to generate an image of the scanned portion of each of the retinas. Wavelengths emitted by optical radiation source 110 may include, for example, 840 nm, 852 nm, and 1060 nm, as well as wavelengths between 632 nm-1 micron. Often times, the optical radiation emitted by optical radiation source 110 may be in the near-infrared portion of the electromagnetic spectrum, but this need not always be the case. In some instances, optical radiation source 110 may include a super continuum light source or an array of laser diodes (or other light sources) configured to emit optical radiation at more than one wavelength. In such cases, optical radiation in the infrared spectrum (e.g., 840 nm) could be used to image the retina, while optical radiation in the visible spectrum (e.g., 535 nm) could be used to deliver stimuli to the subject (e.g., stimuli to generate a fixation target). An advantage of using infrared light to image the retina as compared to using visible light is that the maximum permissible exposure to infrared light is higher than visible light, allowing light of a higher intensity to be safely delivered into the eye to image the retina. Optical radiation source 110 may be coupled to optical transmission medium 115 (e.g., optical fiber) within which the optical radiation propagates towards fiber coupler 120. Splitter 125 of fiber coupler 120 may split the optical radiation into two components. A first component of the optical radiation may propagate via optical transmission medium 127 (e.g., optical fiber) towards right eye optics 130, while a second component of the optical radiation may propagate via optical transmission medium 127' (e.g., optical fiber) towards left eye optics 135. In some instances, fiber coupler 120 may be a 50/50 fiber coupler that splits the optical radiation into two components having equal power. While the following description focuses on right eye optics 130 for conciseness, it is understood that a similar description may apply to left eye optics 135.

Right eye optics 130 may include acousto-optic modulator (AOM) 140 (i.e., an optical switch). The output intensity of AOM 140 may be continuously controlled by the voltage output from a digital to analog converter (DAC) (not depicted). As the beam raster-scans the retina, the DAC drives the AOM to modulate the optical radiation source so that the optical radiation may only transmitted through the AOM during the central 80% of the forward sweep of the scanning cycle, thereby limiting the exposure to only those times when the optical radiation is being detected. AOM 140 may also be used to modulate the power of the optical radiation to place any gray-scale image point-by-point onto the retina. A stimulus presented in this way appears in negative contrast (i.e., optical radiation is switched off to write the stimulus) on the image raster-scanned on the retina. Since the AOM is synchronized with the scanning of the beam, modulation timing can be manipulated to place a stimulus at any location within the raster scan. In this manner, the imaging and stimulus delivery may be performed using the same source of optical radiation. In one embodiment, an AOM from Brimrose Corporation of Sparks, MD may be used in binocular SLO 100.

Optical radiation from AOM 140 may be carried via optical transmission medium 142 to fiber collimator 145, which collimates the incident optical radiation into a beam of optical radiation. In some instances, the collimated beam may directly propagate to beam splitter 175, while in other instances, the collimated beam may pass through an aperture and/or pinhole 176 that may filter and/or limit the amount of radiation and/or the diameter of the beam before the beam reaches beam splitter 175.

Beam splitter 175 may transmit the collimated beam to microelectromechanical systems (MEMS) device 150, which may be mounted on a tip/tilt stage. In some instances, beam splitter 175 may further define and/or delimit the diameter of the collimated beam and/or filter the wavelengths transmitted therethrough (in which case beam splitter 175 may also be a dichromatic filter). Over time, MEMS device 150 may adjust a position of the beam incident on the subject's retina so that a region of the subject's retina may be scanned, preferably in the X and Y dimensions. The scanning performed by MEMS device 150 may be a raster scan of a portion of the subject's retina that is of interest, and may have a slow- and fast-scan rate of between 60 Hz and 23.5 kHz, respectively. MEMS device 150 may have an optical scan angle up to 15 degrees. In many instances, the movement and/or operation of first MEMS device 150 may be controlled by the power (e.g., voltage) delivered thereto. The means for controlling MEMS device 150 has not been depicted for conciseness.

While MEMS device 150 is used in the preferred embodiment, other scanning mechanisms may be employed. For instance, a resonant scanner may be used in place of MEMS device 150 that is able to scan at, for example, 15-16 kHz (such as an EOPC SC30 from Electro-Optical Products Corporation of Ridgewood, NY, which has a mirror size of approximately 3×4 mm). As another example, a galvanometer scanner may be used in place of MEMS device 150 that is capable of performing a 30 Hz scan and is capable of generating a clean saw tooth wave (such as a Cambridge technologies 60 Hz galvanometer scanner with a working aperture of approximately 6 mm). A MEMS scanner, however, is preferred, as it is often times smaller in size and lighter weight than other bi-directional scanners.

The optical radiation reflected by MEMS device 150 may be incident on lens 155, which may focus the optical radiation incident thereon to a point at, or near, a surface of mirror 160. In some embodiments, mirror 160 may be a flat plane mirror and/or a fold mirror, and may be mounted on a tip/tilt stage. Mirror 160 may direct optical radiation incident thereon to lens 165, which configures a diameter of the beam incident thereon to approximately a diameter of the subject's pupil (e.g., the diameter measuring 2-4 mm). The distance of the optical path between lens 155 and lens 165 may be the sum of the respective focal lengths of the two lenses 155, 165.

The subject's right eye 170 (i.e., a lens of the subject's right eye) focuses the incident beam of optical radiation to a point on the subject's retina (i.e., in the back of the subject's eye). When optical radiation is reflected from the subject's retina, it travels a path similar to the incident optical radiation, except in reverse (in particular being de-scanned by MEMS device 150), until the optical radiation reflected from the subject's retina is incident upon beam splitter 175. Once incident upon beam splitter 175, the reflected optical radiation may be directed to lens 178, which focuses the optical radiation incident thereon to a point (which at times may be referred to as a retinal conjugate) upon optical fiber coupling 180 (or other device) adapted to transmit the focused optical radiation to optical transmission medium 182 (e.g., optical fiber) and, ultimately, to detector 185, which is sensitive to the optical radiation emitted by optical radiation source 110. Lens 178, optical fiber coupling 180, optical transmission medium 182, and detector 185 may form a detector assembly.

In some instances, detector 185 may be constructed using a photomultiplier tube (PMT) and/or an avalanche photodiode (APD) light detector that converts the optical signal into an electrical signal. One example of a PMT is a Hamamatsu PMT from Hamamatsu Photonics K.K. of Hamamatsu City, Shizuoka, Japan. Additionally, or alternatively, detector 185 may be a photographic detector (e.g., a charge-coupled device (CCD) image sensor) capable of capturing an image of the subject's retina.

Left eye optics 135 may include components similar to right eye optics 130, including AOM 140', optical transmission medium 142', fiber collimator 145', aperture/pinhole 176', beam splitter 175', MEMS device 150', lens 155', mirror 160', lens 165', lens 178', optic fiber coupling 180', optical transmission medium 182', and detector 185'. These components may operate and function in a manner similar to those of right eye optics 130 with the exception of an orientation and/or positioning of some of the components so as to accommodate a different location of the subject's left eye 170'.

In some instances, binocular SLO 100 may include an onboard memory (not depicted) coupled to first and second detectors 185 and 185' and that is configured to record the signals detected by first and second detectors 185 and 185'. Additionally, or alternatively, the onboard memory may be configured to store one or more instructions to be executed by an onboard processor (not shown) that may control the operation of one or more components of system 100 (e.g., AOM 140, MEMS device 150). Additionally, or alternatively, binocular SLO 100 may also include a transceiver (wired and/or wireless) (not depicted in FIG. 1) that may communicate information detected by first and second detectors 185 and 185' and/or stored in the onboard memory. In some instances, the transceiver may receive instructions regarding an operation of binocular SLO 100 and/or an adjustment to a configuration of one or more components of binocular SLO 100.

In one embodiment, binocular SLO 100 may be configured and/or adapted to generate a 512×512 pixel image of the subject's retina(s) using a light wavelength of, for example, 840 nm and a retinal scan of +/−3.6 degrees. In some instances, binocular SLO 100 may provide a telescopic magnification of, for example, 3.5×. In some embodiments, a clear aperture of the MEMS device 150 included in the binocular SLO 100 may result in a field of view (FOV) of 7.2 degrees (which in turn limits the retinal scan to +/−3.6 degrees). Such FOV may be smaller than the FOV of a typical fundus picture. In some cases, this restricted FOV may be due to one or more physical limitations of the MEMS device 150 that has a 1.2 mm clear aperture, of which approximately two-thirds may be used because of the way the MEMS device 150 may be mounted at an angle with respect to the optical path. Nevertheless, the FOV may be adjusted independently of MEMS device 150, such as by adjusting the magnification of the Keplerian telescope (i.e., including the magnification of lens 155 and 165). In general, a larger FOV is preferable, as a larger FOV permits the tracking of larger degrees of motion for each eye. As the eye motion of more neurologically damaged patients is often greater, a larger FOV permits the tracking of fixational eye movement for more neurologically damaged patients. While a larger FOV is preferable for eye motion tracking, a higher FOV unfortunately lowers the resolution of the retinal image. Having a 7.2 degree FOV is a good compromise—it allows for the median microsaccade velocity to occur without losing real-time stabilization and eye tracking capabilities, and provides high resolution images (i.e., much higher resolution than a typical fundus camera with a 30 degree of FOV or more).

In some embodiments, one or more components of binocular SLO 100 may be adjustable. For example, a positioning of lenses 165 and/or 165' and/or an operation of first and/or second MEMS device 150 and/or 150' may be adjustable so as to facilitate directing the beam incident on the lens of the subject's right and/or left eye 170 and/or 170' in such a way that the beam focuses on the subject's retina(s).

Additionally, in some instances, a variable power liquid lens may be employed. These adjustments may be made in order to, for example, accommodate abnormalities (e.g., astigmatism, near sightedness and/or far sightedness) in the shape or focus of the subject's eye(s) 170 and/or 170'. Variable power liquid lenses may be used in place of lenses 165/165', or may be inserted between beam splitter 175/175' and MEMS device 150/150' (or any location where the optical beam is collimated).

In some instances, binocular SLO 100 may also include one or more mechanisms (e.g., inter-pupillary distance (IPD) adjustment mechanism 183) to enable adjustment of a position of right eye optics 130 relative to a position of left eye optics 135. In some cases, these mechanisms may be used to increase and/or decrease a distance therebetween so as to accommodate subjects with varying inter-pupillary distances. Further details of IPD adjustment mechanism 183 are provided below with respect to FIG. 3.

In some cases, binocular SLO 100 may also include one or more attachments that enable the positioning of the system and/or a portion thereof near the subject's eye (or eyes) so that measurements may be taken. In some cases, these attachments may include a strap, shelf, bar, and/or stabilization mechanism (not depicted).

In some cases, binocular SLO 100 may also include one or more stabilization mechanisms that are coupled to first and/or second detectors 185 and/or 185', and/or a stabilization program (e.g., software) may be applied to the received and/or recorded detected signals and/or images generated therefrom.

Figure 2:
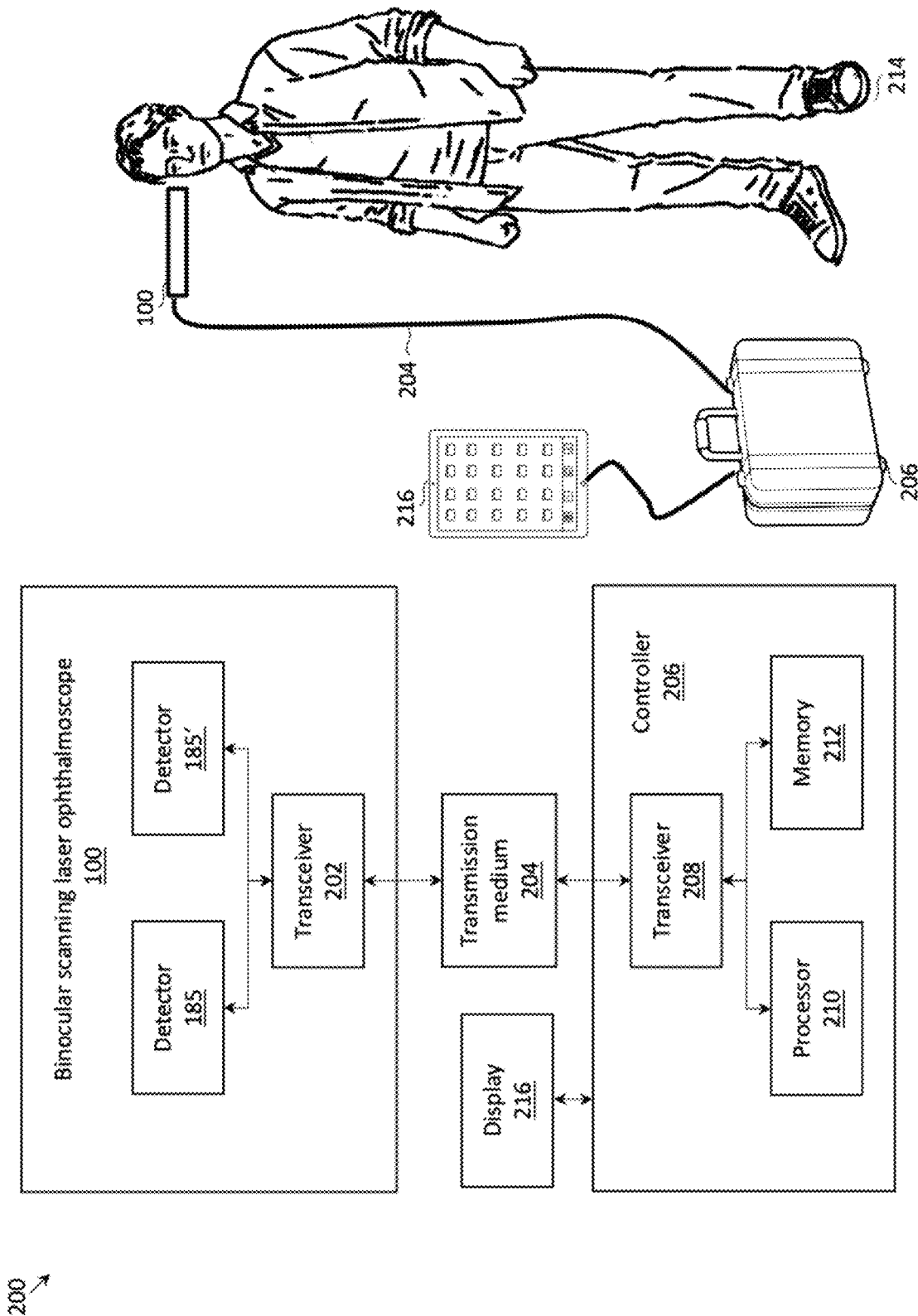
FIG. 2 depicts a binocular system, including a binocular SLO and a controller, in accordance with one embodiment of the invention.

FIG. 2 depicts binocular system 200 with binocular SLO 100 communicatively coupled to controller 206 via transmission medium 204. Most of the details of SLO 100 have been abstracted away for ease of illustration, except for detectors 185/185'. Detectors 185/185' may be communicatively coupled to transceiver 202 which, together with transceiver 208, is configured to transmit signals to and/or receive signals from controller 206 via transmission medium 204. In particular, transceiver 202 may be configured to transmit images of the left and right retinas to transceiver 208 of controller 206. In the example depicted on the right side of FIG. 2, the transmission medium may be a cable (e.g., copper cable, optical cable), while in another embodiment, binocular SLO 100 may communicate wirelessly with controller 206, in which case transmission medium 204 may be a wireless communication channel.

Controller 206 may include processor 210 (e.g., an FPGA) and memory 212, and processor 210 may receive images of the left and right retina from transceiver 208. In some embodiments, the initial images (of each of the retinas) may be used as reference images by processor 210, and subsequent images (of each of the retinas) may be spatially aligned by processor 210 with the initial images (e.g., using techniques such as mean squared error, correlation, etc.) in order for processor 210 to determine the fixational eye movement of each of the eyes. It is noted that the reference image may be a two-dimensional image and subsequent two-dimensional images may be registered with the two-dimensional reference image in order to determine fixational eye movement. Alternatively, the reference image may be a two-dimensional image, but subsequent images may each be a strip (i.e., a single line of a raster scan), and the strips could be registered to the two-dimensional reference image in order to determine fixational eye movement. Plots of the fixational eye movement of each of the eyes may be displayed to the operator of binocular system 200 (e.g., via display 216 of a tablet computer). The fixational eye movement that is measured may include microsaccades as well as slower drift movements. Further, processor 210 may determine the extent to which the fixational motion of the right eye deviates from the fixation motion of the left eye (e.g., by calculating a difference). Such deviation measurement may also be displayed to the operator of binocular system 200 (e.g., via display 216). Memory 212 may store instructions that, when executed by processor 210, cause processor 210 to perform the stated operations of the processor.

The right side of FIG. 2 depicts the relative sizes of binocular SLO 100 and controller 206 (e.g., relative to one another, and relative to the approximate size of human subject 214). In a preferred embodiment, the size and weight of binocular SLO 100 permits binocular SLO 100 to be held by subject 214 (or a medical professional administering an exam of the eyes of subject 214). For example, binocular SLO 100 may measure 30 cm×60 cm and may weigh less than 20 pounds. In another embodiment, binocular SLO 100 may be mounted on, for example, a table and/or tripod (not depicted).

Controller 206 may be packaged into a briefcase (or another portable packaging). In some embodiments, the processing may be performed locally on controller 206, while in other embodiments, the controller 206 may act as a relay between binocular SLO 100 and a server (not depicted), and the processing of data may be performed on the server (e.g., in the cloud).

Figure 3A:
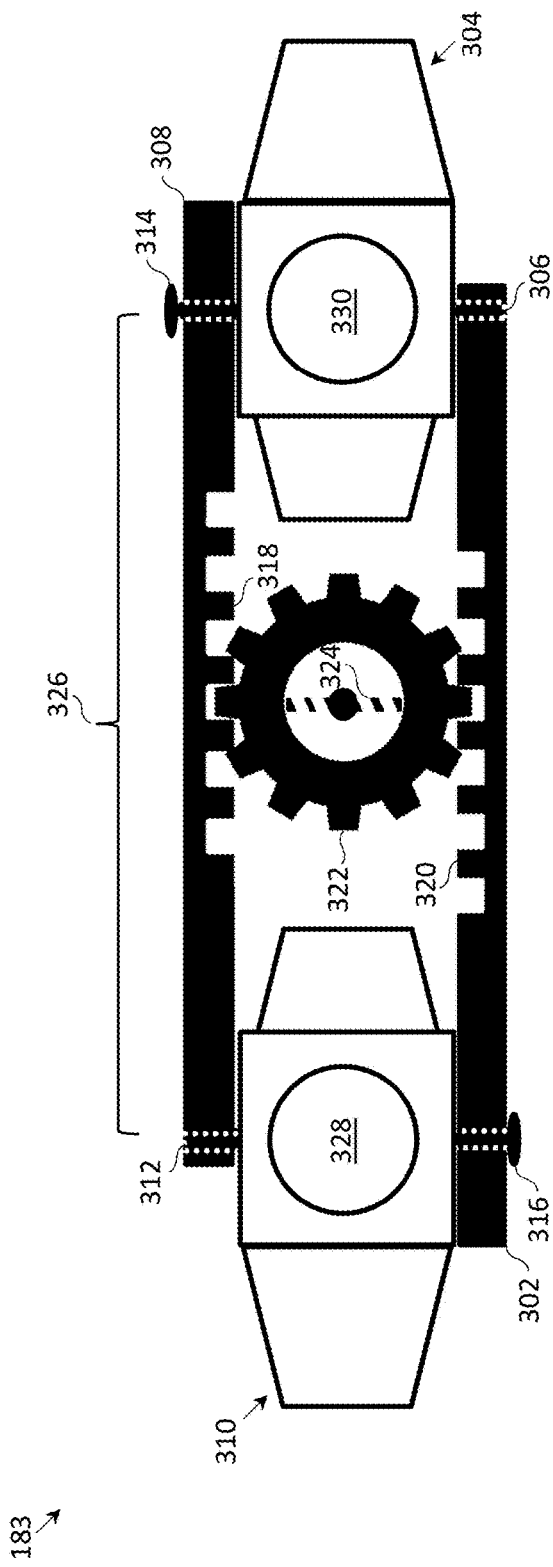
FIG. 3A depicts a front view of an inter-pupillary distance (IPD) adjustment mechanism, in accordance with one embodiment of the invention.

FIG. 3A depicts a front view of inter-pupillary distance (IPD) adjustment mechanism 183 (depicted together with housing 310 for left eye optics 135 and housing 304 for right eye optics 130), in accordance with one embodiment of the invention.

IPD adjustment mechanism 183 may include bottom control arm 302 that is fixedly attached to housing 304 via static pin 306. Static pin 306 may protrude from housing 304 and be inserted into a pin hole of bottom control arm 302. There may be an adhesive applied to the pin hole of bottom control arm 302 that keeps static pin 306 anchored within the pin hole of bottom control arm 302. IPD adjustment mechanism 183 may also include top control arm 308 that is fixedly attached to housing 310 via static pin 312. Static pin 312 may protrude from housing 310 and may be inserted into a pin hole of top control arm 308. There may be an adhesive applied to the pin hole of top control arm 308 that keeps static pin 312 anchored within the pin hole of top control arm 308.

Headed pin 314 may also protrude from housing 304. In contrast to static pin 306, headed pin 314 may linearly slide within slot 334 (not visible in the front view of FIG. 3A, but visible in the top view of FIG. 3B) of top control arm 308. Headed pin 316 may also protrude from housing 310. Similarly, headed pin 316 may linearly slide within a slot (not visible in the front view of FIG. 3A) of bottom control arm 302.

Grooves 318 of top control arm 308 may be mechanically coupled to grooves 320 of bottom control arm 302 via gear 322. When gear 322 is rotated in a clockwise manner, housing 304 and housing 310 are translated towards one another, in turn decreasing IPD 326 which separates left eye port 328 from right eye port 330. When gear 322 is rotated in a counter-clockwise manner, housing 304 and housing 310 are translated away from one another, in turn increasing the IPD 326 which separates left eye port 328 from right eye port 330. Friction screw 324 may adjust the ease at which gear 322 may be rotated. If gear 322 is too easily rotated, IPD 326 may not be stable over time, while if the rotation of gear 322 is very difficult, IPD 326 may only be adjusted with much effort. Therefore, friction screw 324 may be calibrated to allow gear 322 to rotate with a moderate amount of torque.

Figure 3B:
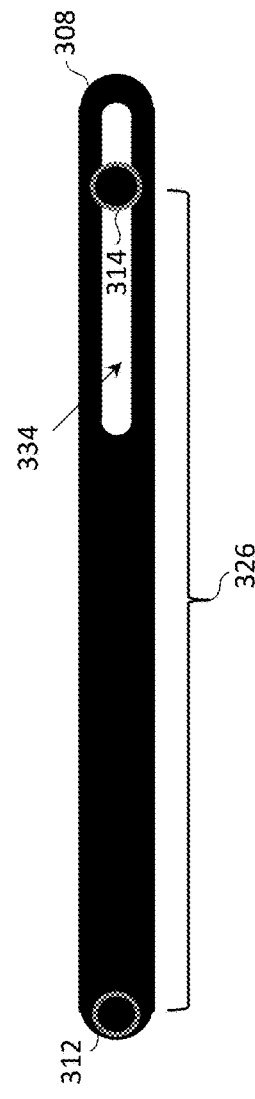
FIG. 3B depicts a top view of the IPD adjustment mechanism, in accordance with one embodiment of the invention.

FIG. 3B depicts a top view of IPD adjustment mechanism 183 (in which housing 328, 330 is not depicted for conciseness). Visible in the top view are static pin 312, top control arm 308 and headed pin 314. Headed pin 314 may be lodged within slot 334, allowing headed pin and top control arm 308 to slide in a linearly manner with respect to one another.

Figure 3C:
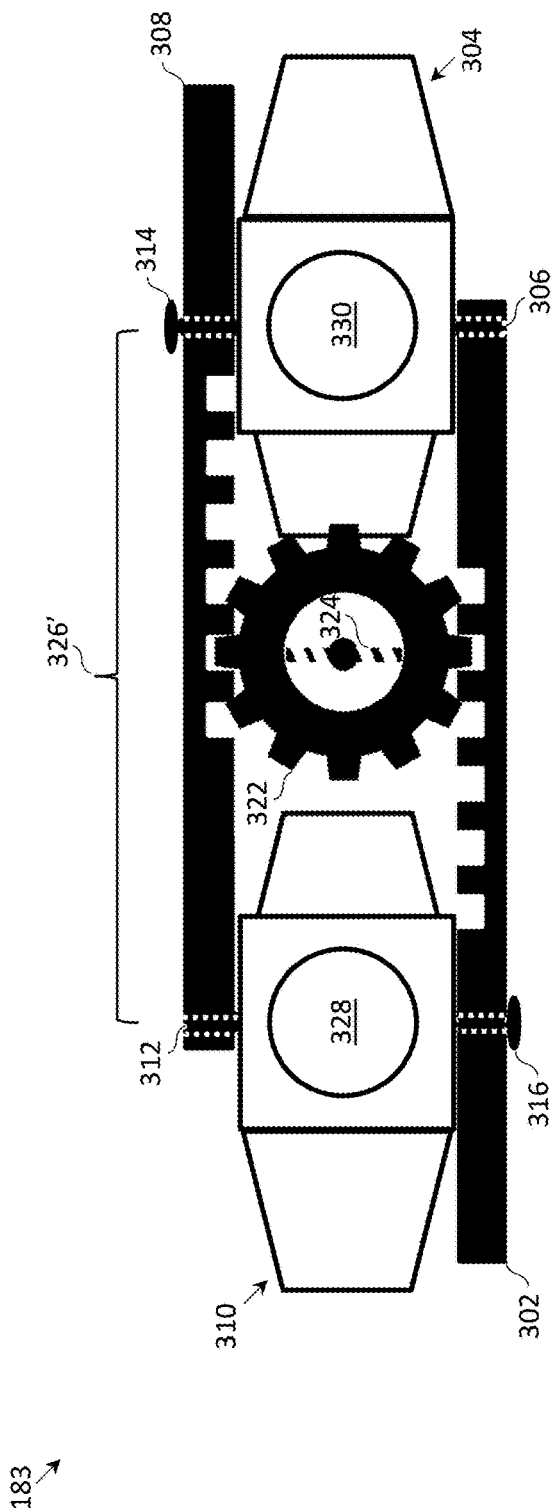
FIG. 3C depicts a front view of the IPD adjustment mechanism with the IPD decreased, in accordance with one embodiment of the invention.

FIG. 3C depicts another front view of IPD adjustment mechanism 183, in which gear 322 has been rotated in a clockwise direction with respect to the position of gear 322 in the front view of FIG. 3A. When FIG. 3C is compared to FIG. 3A, one will notice that IPD 326' is less than IPD 326, demonstrating how the rotation of gear 322 in the clockwise direction decreases the IPD.

Figure 3D:
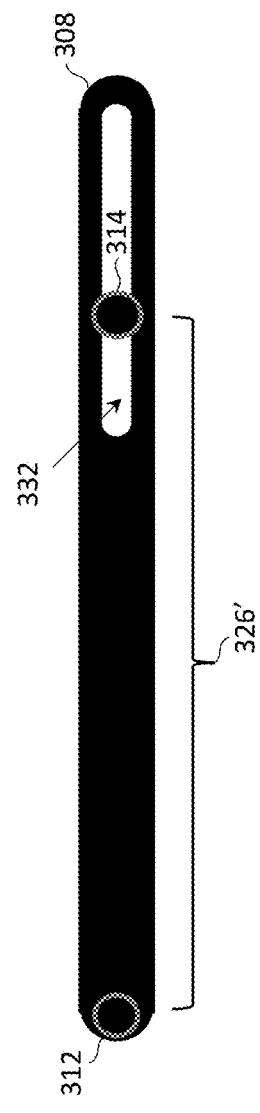
FIG. 3D depicts a top view of the IPD adjustment mechanism with the IPD decreased, in accordance with one embodiment of the invention.

FIG. 3D depicts a top view of IPD adjustment mechanism 183 when gear 322 is located in the position of FIG. 3C. When FIG. 3D is compared to FIG. 3B, one should be able to appreciate how headed pin 314 slides within slot 334. The linear translation of headed pins 314, 316 within their respective slots effectively limits the displacement of housing 304 and 310 to also be linear (i.e., limited to motion within a single plane). The displacement of housing 304 and 310 being restricted to one plane removes any need to calibrate the right (left) eye optics rotationally about the optical axis of the right (left) eye, thereby simplifying the design of the right (left) eye optics, respectively. If not already apparent, the instant linear IPD adjustment mechanism 183 is distinct from the hinged IPD adjustment mechanism of many binoculars, which do have a rotational component.

Figure 4:
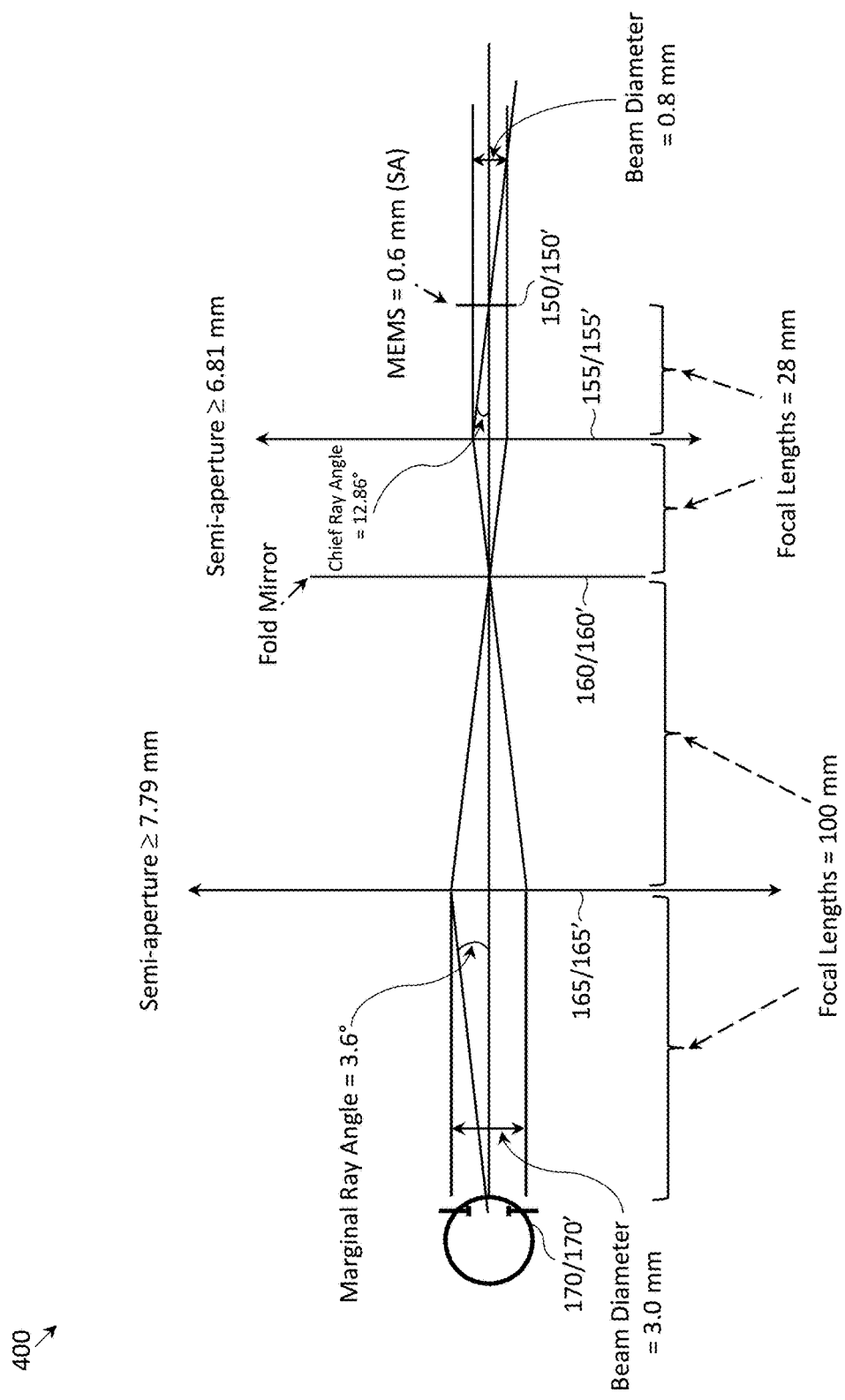
FIG. 4 depicts an optical ray tracing schematic of an afocal system, in accordance with one embodiment of the invention.

FIG. 4 depicts optical ray tracing schematic 400 of an exemplary afocal system, in accordance with one embodiment of the invention. More specifically, ray tracing schematic 400 shows a beam of optical radiation passing through components of either right eye optics 130 or left eye optics 135. The initial beam has an approximate diameter of 0.8 mm that is incident upon a MEMS device 150 (or 150') with a 0.6 mm Semi Aperture (SA). More generally, the MEMS device 150 may have a SA of 0.6-0.75 mm. The beam with, for example, a chief ray angle of 12.86° then passes through lens 155 (or 155'), which, in this instance, has a semi-aperture (i.e., a radius) of greater than or equal to 6.81 mm. The beam is then incident on mirror 160 (or 160') (in this instance a fold mirror) and proceeds to lens 165 (or 165'), which, in this instance, has a semi-aperture of greater than or equal to 7.79 mm. The beam, which is now collimated with a marginal ray angle of, for example, 3.6° will reach the subject's eye 170 (or 170') with a beam diameter of 3 mm. The marginal ray angle of 3.6° may enable a full retinal scan of 7.2°, in which each degree of retinal scanning is able to image a retinal distance of about 291 microns for the standard human eye. The focal length of lens 155 (or 155') may measure 28 mm, while the focal length of lens 165 (or 165') may measure 100 mm. In another embodiment, the previously discussed variable power liquid lens of the binocular SLO may be configured to accommodate for a flexible eye relief of between 100-200 mm (i.e., distance between lens 165/165' and the subject's pupils).

Figure 5:
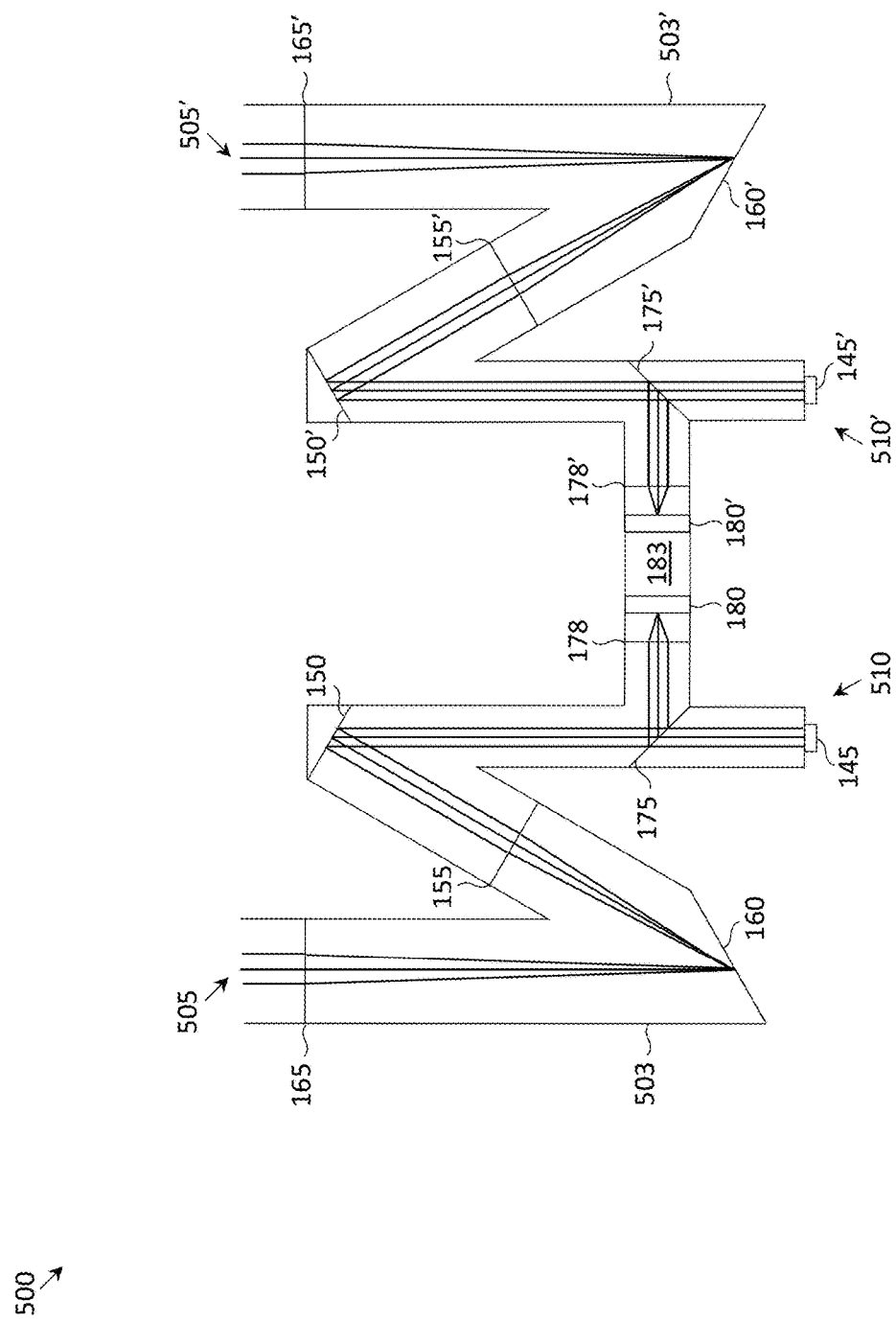
FIG. 5 depicts a cross-section of a portion of a binocular SLO, in accordance with one embodiment of the invention.

FIG. 5 depicts a cross-section of a portion of a binocular SLO, including ray tracing of the optical paths. At a high level, the cross-section includes housing 503 (housing the right eye optics) separated from housing 503' (housing the left eye optics) by IPD adjustment mechanism 183. Optical radiation may enter end portion 510 of housing 503 via fiber collimator 145. The optical radiation may pass through beam splitter 175 before being reflected off of MEMS device 150. The optical radiation may then be focused by lens 155, reflected off of mirror 160, and focused by lens 165, before exiting housing 503 at end portion 505 (which is located proximate to the subject's right eye when binocular SLO is in use). Optical radiation that is reflected off of the subject's right retina enters into housing at end portion 505, is focused by lens 165, reflected off of mirror 160, focused by lens 155, de-scanned by MEMS device 150, reflected by beam-splitter 175, and focused by lens 178, before being incident on optical fiber coupling 180. Optical transmission medium 182 and detector 185 are not depicted in the cross-section of FIG. 5. A similar description applies to housing 503', which houses the left eye optics 135 of the binocular SLO.

Figure 6:
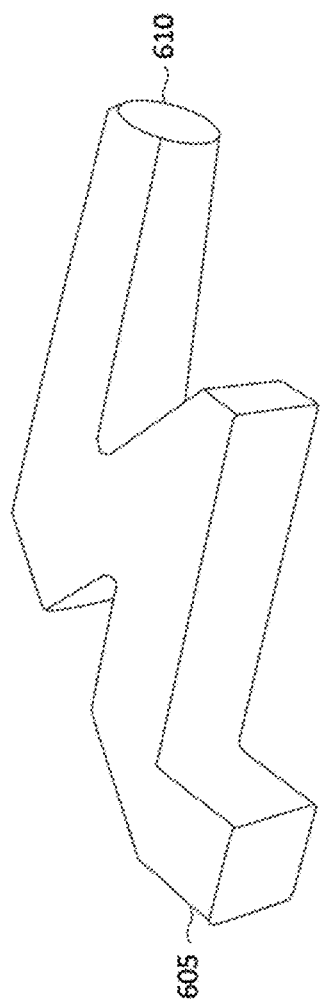
FIG. 6 depicts a perspective view of a housing for containing the right eye optics of a binocular SLO, in accordance with one embodiment of the invention.

FIG. 6 depicts a perspective view of housing 600 for containing the right eye optics (or a portion thereof) of a binocular SLO, in accordance with one embodiment of the invention. Housing 600 includes opening 610 configured for placement at, or near, the subject's right eye so that optical radiation may be directed into the subject's right eye and received therefrom and end portion 605 configured to be coupled to fiber 142.

In some embodiments, when, for example, the optical radiation source 110 is included within housing 500, end portions 510, 510' may not be coupled to fibers 142, 142', respectively, and instead may house a portion of optical radiation source 110 and/or fiber coupler 120. Likewise, when optical radiation source 110 is included in housing 600, end portion 605 may not be coupled to fiber 142, and instead may house a portion of optical radiation source 110 and/or fiber coupler 120.

Optionally, binocular system 200 may have a pupil camera (or other type of imaging capability) in order to properly and quickly align the eyes of a patient with respect to binocular SLO 100. In some embodiments, the pupil camera may not be part of the optical design of binocular SLO 100 (i.e., is not used for imaging the retina of the eye), but rather is only used for the proper placement of a patient's eye.

Figure 7:
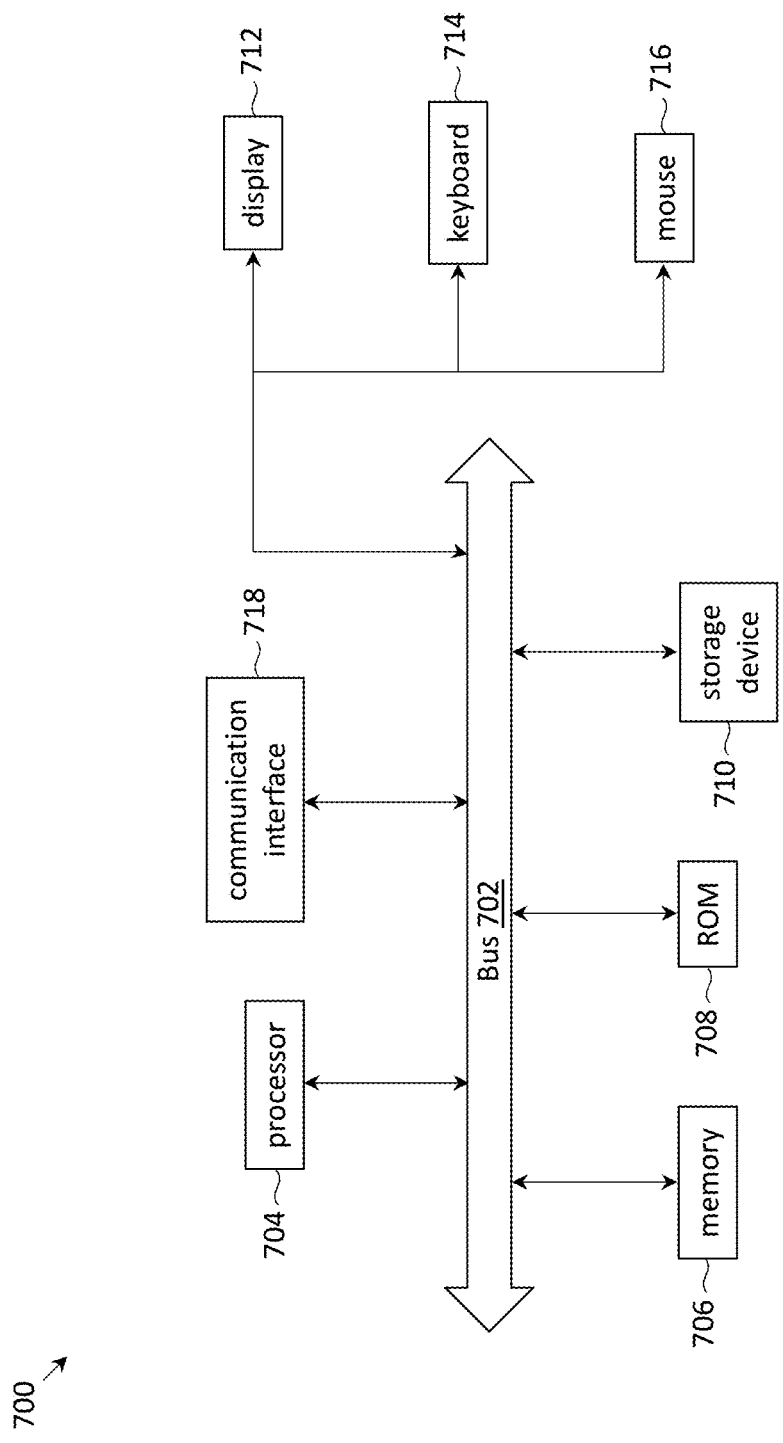
FIG. 7 depicts components of a computer system in which computer readable instructions instantiating the methods of the present invention may be stored and executed.

As is apparent from the foregoing discussion, aspects of the present invention involve the use of various computer systems and computer readable storage media having computer-readable instructions stored thereon. FIG. 7 provides an example of a system 700 that may be representative of any of the computing systems (e.g., controller 206) discussed herein. Examples of system 700 may include a smartphone, a desktop, a laptop, a mainframe computer, an embedded system, etc. Note, not all of the various computer systems have all of the features of system 700. For example, certain ones of the computer systems discussed above may not include a display inasmuch as the display function may be provided by a client computer communicatively coupled to the computer system or a display function may be unnecessary. Such details are not critical to the present invention.

System 700 includes a bus 702 or other communication mechanism for communicating information, and a processor 704 coupled with the bus 702 for processing information. Computer system 700 also includes a main memory 706, such as a random-access memory (RAM) or other dynamic storage device, coupled to the bus 702 for storing information and instructions to be executed by processor 704. Main memory 706 also may be used for storing temporary variables or other intermediate information during execution of instructions to by processor 704. Computer system 700 further includes a read only memory (ROM) 708 or other static storage device coupled to the bus 702 for storing static information and instructions for the processor 704. A storage device 710, for example a hard disk, flash memory-based storage medium, or other storage medium from which processor 704 can read, is provided and coupled to the bus 702 for storing information and instructions (e.g., operating systems, applications programs and the like).

Computer system 700 may be coupled via the bus 702 to a display 712, such as a flat panel display, for displaying information to a computer user. An input device 714, such as a keyboard including alphanumeric and other keys, may be coupled to the bus 702 for communicating information and command selections to the processor 704. Another type of user input device is cursor control device 716, such as a mouse, a trackpad, or similar input device for communicating direction information and command selections to processor 704 and for controlling cursor movement on the display 712. Other user interface devices, such as microphones, speakers, etc. are not shown in detail but may be involved with the receipt of user input and/or presentation of output.

The processes referred to herein may be implemented by processor 704 executing appropriate sequences of computer-readable instructions contained in main memory 706. Such instructions may be read into main memory 706 from another computer-readable medium, such as storage device 710, and execution of the sequences of instructions contained in the main memory 706 causes the processor 704 to perform the associated actions. In alternative embodiments, hard-wired circuitry or firmware-controlled processing units may be used in place of or in combination with processor 704 and its associated computer software instructions to implement the invention. The computer-readable instructions may be rendered in any computer language.

In general, all of the above process descriptions are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 700 or similar electronic computing device, that manipulates and transforms data represented as physical (electronic) quantities within its registers and memories into other data similarly represented as physical quantities within its memories or registers or other such information storage, transmission or display devices.

Computer system 700 also includes a communication interface 718 coupled to the bus 702. Communication interface 718 may provide a two-way data communication channel with a computer network, which provides connectivity to and among the various computer systems discussed above. For example, communication interface 718 may be a local area network (LAN) card to provide a data communication connection to a compatible LAN, which itself is communicatively coupled to the Internet through one or more Internet service provider networks. The precise details of such communication paths are not critical to the present invention. What is important is that computer system 700 can send and receive messages and data through the communication interface 718 and in that way, communicate with hosts accessible via the Internet. It is noted that the components of system 700 may be located in a single device or located in a plurality of physically and/or geographically distributed devices.

Thus, a binocular retinal imaging device for tracking fixational eye motion has been described. It is to be understood that the above-description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A binocular system, comprising:
   a binocular scanning laser ophthalmoscope (SLO) comprising:
      right eye optics configured to generate a plurality of images a retina of a right eye of a subject, wherein the right eye optics comprise:
         a first acousto-optic modulator (AOM) configured to selectively attenuate a first beam of optical radiation;
         a first fiber collimator configured to receive the first beam from the first AOM;
         a first beam splitter configured to pass the first beam from the first fiber collimator to a first MEMS device and reflect the first beam towards a first detector assembly;
         the first MEMS device configured to scan the first beam along a first and second dimension at a scan rate and to de-scan the first beam onto the first beam splitter;
         a first lens configured to focus the first beam onto a first mirror and to focus the first beam onto the first MEMS device;
         the first mirror configured to direct the first beam towards the first lens and towards a second lens;
         the second lens configured to focus the first beam into the right eye of the subject, the second lens further configured to focus the first beam reflected from the retina of the right eye of the subject onto the first mirror; and
         the first MEMS device further configured to de-scan the first beam onto the first beam splitter;
      left eye optics configured to generate a plurality of images a retina of a left eye of the subject, wherein the left eye optics comprise:
         a second AOM configured to selectively attenuate a second beam of optical radiation;
         a second fiber collimator configured to receive the second beam from the second AOM;
         a second beam splitter configured to pass the second beam from the second fiber collimator to a second MEMS device;
         the second MEMS device configured to scan the second beam along the first and second dimension at the scan rate and de-scan the second beam onto the second beam splitter:
         a third lens configured to focus the second beam onto a second mirror and the second MEMS device;
         the second mirror configured to direct the second beam towards the third lens and a fourth lens;
         the fourth lens configured to focus the second beam into the left eye of the subject, the fourth lens further configured to focus the second beam reflected from the retina of the left eye of the subject onto the second mirror;
         the second mirror further configured to direct the second beam towards the third lens; and
         the second beam splitter further configured to reflect the second beam towards a second detector assembly and
      a processor configured to:
         determine movement of the right eye based on the plurality of images of the retina of the right eye of the subject;

determine movement of the left eye based on the plurality of images of the retina of the left eye of the subject; and generate a signal representative of a deviation between the movement of the right eye and the movement of the left eye.

2. The binocular system of claim 1, wherein the plurality of images of the retina of the right eye have a point of view similar to a point of view for the images of the retina of the left eye.

3. The binocular system of claim 1, wherein a resolution of the plurality of images of the retina of the right eye is similar to a resolution for the plurality of images of the retina of the left eye.

4. The binocular system of claim 1, wherein the binocular SLO further comprises:

an inter-pupillary distance (IPD) adjustment mechanism coupled to the right eye optics and the left eye optics, the IPD adjustment mechanism configured to adjust a distance between the right eye optics and the left eye optics.

5. The binocular system of claim 1, wherein the binocular SLO further comprises:

an optical radiation source configured to generate a beam of optical radiation used to generate at least one of the plurality of images of the retina of the left eye of the subject and the plurality of images a retina of a left eye of the subject.

6. The binocular system of claim 5, wherein the optical radiation source comprises a super luminescent diode.

7. The binocular system of claim 1, further comprising:

an acousto-optic modulator (AOM) configured to generate a fixation target for the subject.

8. The binocular system of claim 1, further comprising:

a MEMS device comprising a bi-directional MEMS scanning mirror.

9. The binocular system of claim 1, wherein the binocular SLO further comprises:

an aperture configured to constrain a beam scanning at least one of the retina of the subject's left eye and the retina of the subject's right eye.

10. The binocular system of claim 1, wherein the movement of the right eye is fixational eye movement.

11. The binocular system of claim 1, wherein the movement of the left eye is fixational eye movement.

12. A method comprising:

receiving, by a processor, a plurality of images of the retina of the right eye of the subject and a plurality of images of the retina of the left eye of the subject from a binocular scanning laser ophthalmoscope (SLO) comprising:

right eye optics configured to generate a plurality of images a retina of a right eye of a subject, wherein the right eye optics comprise:

a first acousto-optic modulator (AOM) configured to selectively attenuate a first beam of optical radiation;

a first fiber collimator configured to receive the first beam from the first AOM;

a first beam splitter configured to pass the first beam from the first fiber collimator to a first MEMS device and reflect the first beam towards a first detector assembly;

the first MEMS device configured to scan the first beam along a first and second dimension at a scan rate and to de-scan the first beam onto the first beam splitter;

a first lens configured to focus the first beam onto a first mirror and to focus the first beam onto the first MEMS device;

the first mirror configured to direct the first beam towards the first lens and towards a second lens;

the second lens configured to focus the first beam into the right eye of the subject, the second lens further configured to focus the first beam reflected from the retina of the right eye of the subject onto the first mirror; and the first MEMS device further configured to de-scan the first beam onto the first beam splitter;

left eye optics configured to generate a plurality of images a retina of a left eye of the subject, wherein the left eye optics comprise:

a second AOM configured to selectively attenuate a second beam of optical radiation;

a second fiber collimator configured to receive the second beam from the second AOM;

a second beam splitter configured to pass the second beam from the second fiber collimator to a second MEMS device;

the second MEMS device configured to scan the second beam along the first and second dimension at the scan rate and de-scan the second beam onto the second beam splitter;

a third lens configured to focus the second beam onto a second mirror and the second MEMS device;

the second mirror configured to direct the second beam towards the third lens and a fourth lens;

the fourth lens configured to focus the second beam into the left eye of the subject, the fourth lens further configured to focus the second beam reflected from the retina of the left eye of the subject onto the second mirror;

the second mirror further configured to direct the second beam towards the third lens; and the second beam splitter further configured to reflect the second beam towards a second detector assembly determining, by the processor, movement of the right eye based on the plurality of images of the retina of the right eye of the subject;

determining, by the processor, movement of the left eye based on the plurality of images of the retina of the left eye of the subject;

measuring, by the processor, a deviation between movement of the right eye and movement of the left eye; and generating, by the processor, a signal representative of a deviation between the movement of the right eye and the movement of the left eye.

13. The method of claim 12, wherein the images of the retina of the right eye have a field of view similar to a field of view for the images of the retina of the left eye.

14. The method of claim 12, wherein a resolution of images of the retina of the right eye is similar to a resolution for the images of the retina of the left eye.

15. The method of claim 12, further comprising:

providing, by the controller, a signal representative of a deviation between the movement of the right eye and the movement of the left eye to a display device.

16. The method of claim 12, wherein the movement of the right eye is fixational eye movement.

17. The method of claim 12, wherein the movement of the left eye is fixational eye movement.

18. Computer readable storage media having a set of computer-readable instructions stored thereon, which when executed by the processor cause the processor to:
receive a plurality of images of the retina of the right eye of the subject and a plurality of images of the retina of the left eye of the subject from a binocular scanning laser ophthalmoscope (SLO) comprising:
right eye optics configured to generate a plurality of images a retina of a right eye of a subject, wherein the right eye optics comprise:
a first acousto-optic modulator (AOM) configured to selectively attenuate a first beam of optical radiation;
a first fiber collimator configured to receive the first beam from the first AOM;
a first beam splitter configured to pass the first beam from the first fiber collimator to a first MEMS device and reflect the first beam towards a first detector assembly;
the first MEMS device configured to scan the first beam along a first and second dimension at a scan rate and to de-scan the first beam onto the first beam splitter;
a first lens configured to focus the first beam onto a first mirror and to focus the first beam onto the first MEMS device;
the first mirror configured to direct the first beam towards the first lens and towards a second lens;
the second lens configured to focus the first beam into the right eye of the subject, the second lens further configured to focus the first beam reflected from the retina of the right eye of the subject onto the first mirror; and
the first MEMS device further configured to de-scan the first beam onto the first beam splitter;
left eye optics configured to generate a plurality of images a retina of a left eye of the subject, wherein the left eye optics comprise:
a second AOM configured to selectively attenuate a second beam of optical radiation;
a second fiber collimator configured to receive the second beam from the second AOM;
a second beam splitter configured to pass the second beam from the second fiber collimator to a second MEMS device;
the second MEMS device configured to scan the second beam along the first and second dimension at the scan rate and de-scan the second beam onto the second beam splitter;
a third lens configured to focus the second beam onto a second mirror and the second MEMS device;
the second mirror configured to direct the second beam towards the third lens and a fourth lens;
the fourth lens configured to focus the second beam into the left eye of the subject, the fourth lens further configured to focus the second beam reflected from the retina of the left eye of the subject onto the second mirror;
the second mirror further configured to direct the second beam towards the third lens; and
the second beam splitter further configured to reflect the second beam towards a second detector assembly;
determine movement of the right eye based on the plurality of images of the retina of the right eye of the subject;
determine movement of the left eye based on the plurality of images of the retina of the left eye of the subject;
measure a deviation between movement of the right eye and movement of the left eye;
generate a signal representative of a deviation between movement of the right eye and movement of the left eye; and
provide the signal representative of the deviation between movement of the right eye and movement of the left eye to a display device.

\* \* \* \* \*